(12) United States Patent
Hsiao

(10) Patent No.: US 11,154,633 B2
(45) Date of Patent: Oct. 26, 2021

(54) LIQUID ATOMIZING SYSTEM AND DEVICE ELECTRICALLY CHARGED IN WIRELESS MANNER

(71) Applicant: DONGGUAN YIH TEH ELECTRIC PRODUCTS CO., LTD., Dongguan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 363 days.

(21) Appl. No.: 16/259,833

(22) Filed: Jan. 28, 2019

(65) Prior Publication Data

US 2020/0114037 A1    Apr. 16, 2020

Related U.S. Application Data

(63) Continuation-in-part of application No. 16/157,994, filed on Oct. 11, 2018.

(51) Int. Cl.
    *A61L 9/14*      (2006.01)
    *B05B 17/04*     (2006.01)
    *H02J 7/02*      (2016.01)

(52) U.S. Cl.
    CPC .............. *A61L 9/14* (2013.01); *B05B 17/04* (2013.01); *H02J 7/025* (2013.01); *A61L 2209/11* (2013.01)

(58) Field of Classification Search
    CPC .......... A61L 9/14; A61L 9/22; A61L 2209/11; A61L 2209/132; H02J 50/005; H02J 7/025

USPC ...... 219/387, 433, 450.1; 422/125, 306, 390
See application file for complete search history.

(56) References Cited

U.S. PATENT DOCUMENTS

| | | |
|---|---|---|
| 7,963,460 B2 | 6/2011 | Hsiao |
| 7,992,801 B2 | 8/2011 | Hsiao |
| 8,029,153 B2 | 10/2011 | Hsiao |
| 8,133,440 B2 | 3/2012 | Hsiao |
| 8,196,903 B2 | 6/2012 | Hsiao |
| 8,983,277 B2 | 3/2015 | Hsiao |
| 9,206,963 B2 | 12/2015 | Hsiao |
| 9,410,695 B2 | 8/2016 | Hsiao |
| 9,498,553 B2 | 11/2016 | Hsiao |
| 9,500,358 B2 | 11/2016 | Hsiao |
| 9,844,609 B2 | 12/2017 | Hsiao |
| 10,064,969 B2 | 9/2018 | Hsiao |

(Continued)

FOREIGN PATENT DOCUMENTS

CN    209137472 U  *  3/2018

*Primary Examiner* — Thien S Tran
(74) *Attorney, Agent, or Firm* — Sinorica, LLC

(57) ABSTRACT

A liquid atomizing system electrically charged in a wireless manner: a liquid, a wireless charger, and an atomizer including a wireless charging receiver. The liquid is filled in the atomizer, and the wireless charger is electrically connected with a power source so that an electric power is inputted to the wireless charger from the power source to produce a magnetic field and to send an electromagnetic signal, thus transmitting energy by using the magnetic field. The wireless charging receiver of the atomizer is close to the electromagnetic signal sent by the wireless charger so as to receive the electromagnetic signal and to convert the electromagnetic signal into the electric power for driving the atomizer to atomize the liquid to micro water molecule and to deliver the micro water molecule to an external environment.

13 Claims, 10 Drawing Sheets

(56) References Cited

U.S. PATENT DOCUMENTS

| | | | |
|---|---|---|---|
| 2015/0109823 A1* | 4/2015 | Hsiao | A61L 9/03 362/643 |
| 2015/0117056 A1 | 4/2015 | Hsiao | |
| 2016/0195257 A1 | 7/2016 | Hsiao | |
| 2017/0245679 A1* | 8/2017 | Watts | H05B 6/1236 |

* cited by examiner

LIQUID ATOMIZING SYSTEM AND DEVICE ELECTRICALLY CHARGED IN WIRELESS MANNER

This application is a Continuation-in-Part of application Ser. No. 16/157,994, filed Oct. 11, 2018.

BACKGROUND OF THE INVENTION

Field of the Invention

The present invention relates to a liquid atomizing system and device which are electrically charged in a wireless manner.

Description of the Prior Art

A conventional liquid atomizing device is electrically connected with a power source by using an electrical plug and has electric contacts, but it is easy to cause electric shock. The liquid atomizing device or an electrical wire is connected with a heater of the atomizing device so that the heater heats liquid. After running out the liquid, it is refilled or replaced after a removal of the electrical plug, thus having inconvenient operation.

The present invention has arisen to mitigate and/or obviate the afore-described disadvantages.

SUMMARY OF THE INVENTION

The primary aspect of the present invention is to provide liquid atomizing system and device which are electrically charged in a wireless manner and transmit energy by using a magnetic field so as to convert into electric energy configured to drive the liquid atomizing system and device to atomize the liquid.

Further aspect of the present invention is to provide liquid atomizing system and device which contain a wireless charger including multiple transmitting coil modules so as to electrically charge the system and device and/or various mobile devices or various terminal devices.

Another aspect of the present invention is to provide liquid atomizing system and device which operates easily and safely.

To obtain the above aspects, liquid atomizing system and device electrically charged in a wireless manner provided by the present invention contain: a liquid, a wireless charger, and an atomizer including a wireless charging receiver.

The liquid consists of any one of water, scented liquid, and a mixture of water and scented liquid, wherein the scented liquid is selected from one of aromatic oil, essential oil, essence, aromatic liquid, flower essence, aromatic agent, and fluid which diffuses scent.

The liquid is filled in the atomizer, and the wireless charger is electrically connected with a power source so that an electric power is inputted to the wireless charger from the power source to produce a magnetic field and to send an electromagnetic signal, thus transmitting energy by using the magnetic field. The wireless charging receiver of the atomizer is close to the electromagnetic signal sent by the wireless charger so as to receive the electromagnetic signal and to convert the electromagnetic signal into the electric power for driving the atomizer to atomize the liquid to micro water molecule and to deliver the micro water molecule to an external environment.

The atomizer includes a container, a case, an oscillator, an air conveyor, a main control circuit, and a cap.

The case has an accommodation chamber defined therein and has an opening formed on a top of the accommodation chamber, the wireless charging receiver and the air conveyor are accommodated in the accommodation chamber of the case.

The container abuts against a top of the case so as to shield the opening of the accommodation chamber, the container includes a first groove, a second groove, an air guide portion, a through orifice, and a hollow waterproof structure, wherein the first groove extends to the second groove which communicates with the accommodation chamber, and the first groove receives the liquid, the through orifice is defined between a bottom of the first groove and a top of the second groove, the hollow waterproof structure closes the through orifice from the top of the second groove, the oscillator is received in the hollow waterproof structure and corresponds to the through orifice.

The main control circuit is accommodated in the second groove.

The cap has a nozzle defined on a top thereof and covers the container and the first groove, the air guide portion is arranged on a side of the first groove and has an outlet and an inlet, wherein the outlet communicates with an outer wall of the container and an inner wall of the cap, and the inlet is in communication with the second groove.

The main control circuit is electrically connected with the wireless charging receiver, the oscillator, and the air conveyor, wherein the main control circuit controls the air conveyor and the oscillator to operate.

Thereby, the wireless charger is electrically connected with the power source so that the electric power is inputted to the wireless charger from the power source so as to produce the magnetic field and to send the electromagnetic signal, thus transmitting the energy by using the magnetic field. The wireless charging receiver of the atomizer is close to the electromagnetic signal sent by the wireless charger so as to receive the electromagnetic signal and to convert the electromagnetic signal into the electric power for driving the main control circuit, the oscillator, and the air conveyor, such that the oscillator is turned on to oscillate the liquid flowing into the first groove from the oscillator via the through orifice, thus atomizing the liquid to the micro water molecule. The air conveyor delivers air through the second groove, the inlet, the outlet, a gap between the cap and the first groove to contact with the micro water molecule between the cap and the first groove so that the air transports the micro water molecule to spray toward the external environment from the nozzle.

The wireless charger further includes at least one transmitting coil module. For example, the wireless charger includes multiple transmitting coil modules which are separately arranged in the charge board and are parallelly connected.

DETAILED DESCRIPTION OF THE PREFERRED EMBODIMENTS

Figure 1:
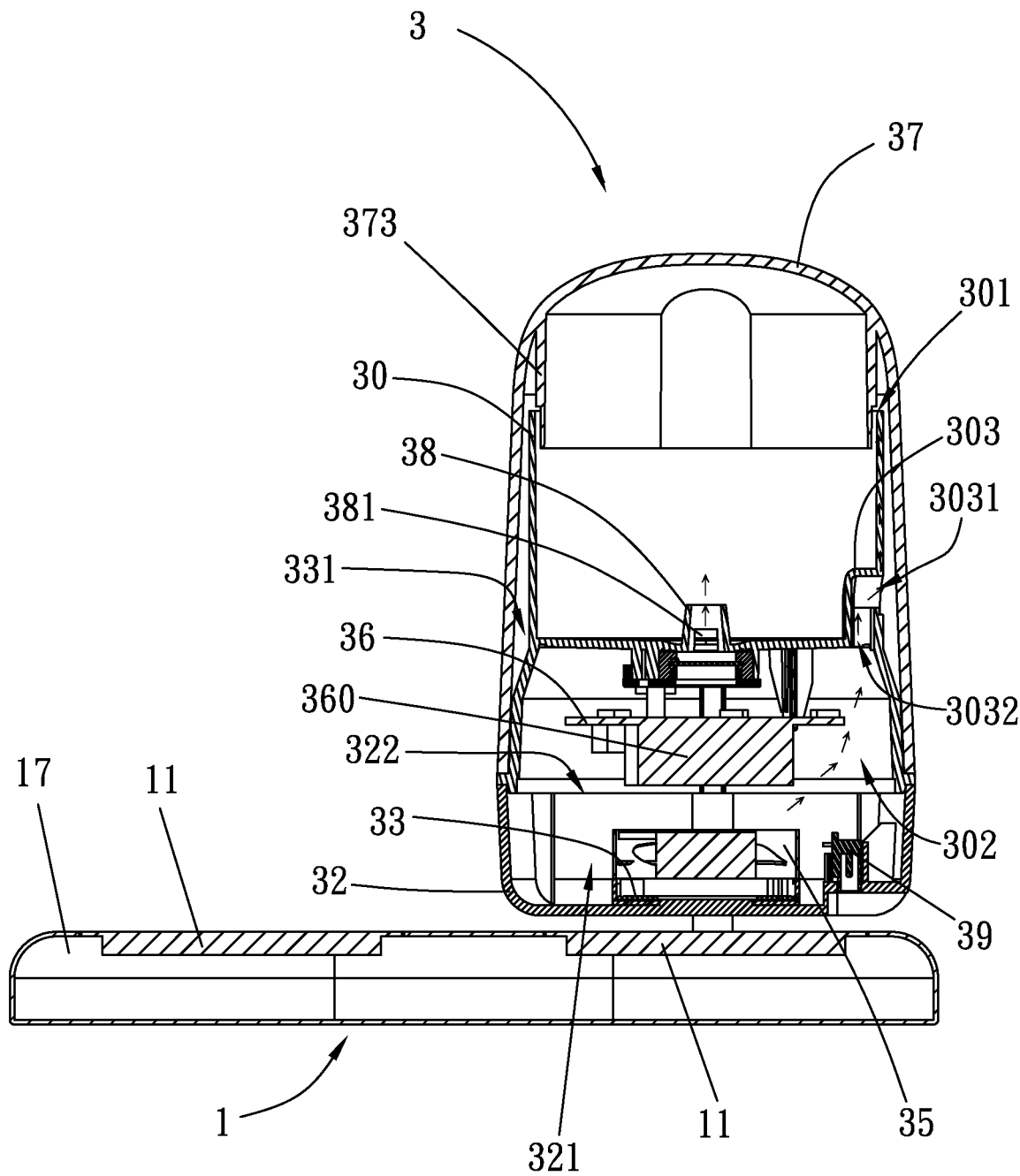
FIG. 1 is a cross sectional view showing the assembly of liquid atomizing system and device electrically charged in a wireless manner according to a preferred embodiment of the present invention.

Liquid atomizing system and device electrically charged in a wireless manner according to a preferred embodiment of the present invention comprise: a liquid consisting of any one of water, scented liquid, and a mixture of water and scented liquid, wherein the scented liquid is selected from one of aromatic oil, essential oil, essence, aromatic liquid, flower essence, aromatic agent, and fluid which diffuses scent.

With reference to FIGS. 1-7, the liquid atomizing system and device electrically charged in the wireless manner according to the preferred embodiment of the present invention further comprise: the liquid (not shown), a wireless charger 1, and an atomizer 3 including a wireless charging receiver 33.

The liquid is filled in the atomizer 3, and the wireless charger 1 is electrically connected with a power source so that an electric power is inputted to the wireless charger 1 from the power source to produce a magnetic field and to send an electromagnetic signal, thus transmitting energy by using the magnetic field. The wireless charging receiver 33 of the atomizer 3 is close to the electromagnetic signal sent by the wireless charger 1 so as to receive the electromagnetic signal and to convert the electromagnetic signal into the electric power for driving the atomizer 3 to atomize the liquid to micro water molecule and to deliver the micro water molecule to an external environment.

Referring to FIGS. 1-7, the atomizer 3 includes a container 30, a case 32, an oscillator 34, an air conveyor 35, a main control circuit 36, and a cap 37. The case 32 has an accommodation chamber 321 defined therein and has an opening 322 formed on a top of the accommodation chamber 321, the wireless charging receiver 33 and the air conveyor 35 are accommodated in the accommodation chamber 321 of the case 32.

The container 30 abuts against the top of the case 32 so as to shield the opening 322 of the accommodation chamber 321. The container 30 includes a first groove 301, a second groove 302, an air guide portion 303, a through orifice 304, and a hollow waterproof structure 305, wherein the first groove 301 extends to the second groove 302 which communicates with the accommodation chamber 321, and the first groove 301 receives the liquid 5, the through orifice 304 is defined between a bottom of the first groove 301 and a top of the second groove 303. The hollow waterproof structure 305 closes the through orifice 304 from a top of the second groove 302, the oscillator 34 is received in the hollow waterproof structure 305 and corresponds to the through orifice 304, and the main control circuit 36 is accommodated in the second groove 302.

The cap 37 has a nozzle 371 defined on a top thereof and covers the container 30 and the first groove 301, the air guide portion 303 is arranged on a side of the first groove 301 and has an outlet 3031 and an inlet 3033, wherein the outlet 3031 communicates with an outer wall of the container 30 and an inner wall of the cap 37, and the inlet 3033 is in communication with the second groove 303.

The main control circuit 36 is electrically connected with the wireless charging receiver 33, the oscillator 34, and the air conveyor 35. The main control circuit 36 is configured to control the air conveyor 35 and the oscillator 34 to operate.

Thereby, the wireless charger 1 is electrically connected with the power source so that the electric power is inputted to the wireless charger 1 from the power source so as to produce the magnetic field and to send the electromagnetic signal, thus transmitting the energy by using the magnetic field. The wireless charging receiver 33 of the atomizer 3 is close to the electromagnetic signal sent by the wireless charger 1 so as to receive the electromagnetic signal and to convert the electromagnetic signal into the electric power for driving the main control circuit 36, the oscillator 34, and the air conveyor 35, such that the oscillator 34 is turned on to oscillate the liquid flowing into the first groove 301 from the oscillator 34 via the through orifice 304, thus atomizing the liquid to the micro water molecule. The air conveyor 35 delivers air through the second groove, the inlet 3033, the outlet 3031, a gap between the cap 37 and the first groove 301 to contact with the micro water molecule between the cap 37 and the first groove 301 so that the air transports the micro water molecule to spray toward the external environment from the nozzle 371.

Referring to FIGS. 1-7, the cap 37 has a shielding extension 373 extending downward from a top of an inner wall of the cap 37 and communicating with the first groove 301 so as to stop the liquid spattering to the gap between the cap 37 and the first groove 301 from the first groove 301. The cap 37 further has an aperture 375 defined on a side of the shielding extension 373 adjacent to the first groove 301, wherein the aperture 375 communicates with the air guide portion 303 and the outlet 302 so as to form an air conduit, such that the air is delivered by the air conveyor 35 to flow through the inlet 3033, the outlet 3031, the gap between the cap 37 and the first groove 301, the aperture 373, an interior of the cap 37, and an interior of the first groove 301 so as to transport the micro water molecule to spray out of the aperture 371 from the first groove 301.

As shown in FIGS. 1, 5 and 7, in an embodiment, the air guide portion 33 has a tube formed in an interior of the atomizer 3, and the external environment is drawn by a fan 35 to flow into a space between container 30 and the cap 37 from the inlet 3033 via outlet 3031.

The air conveyor 35 is any one of the fan, a pump, and a pressure bottle. For example, the air conveyor 35 is the fan, as illustrated in FIGS. 1, 5, and 7.

With reference to FIGS. 1 and 7, the atomizer 3 further includes a hollow pipe 38 formed on and communicating with the through orifice 304 of the first groove 301 so as to deliver vibration waves produced by the oscillator 34.

The atomizer 3 further includes a hole 381 formed on a bottom of the hollow pipe 38 communicating with the through orifice 304 and the hollow pipe 38 so that the liquid in the first groove 301 flows into the oscillator 34 via an upper side of the hollow pipe 38 or the hole 381 and the through orifice 304, wherein a water level of the liquid in the first groove 301 is lower than a height of the hollow pipe 38 so that the liquid flows into the through orifice 304 to contact with the oscillator 34 by using the hole 381, thus oscillating and atomizing the liquid.

Figure 5:
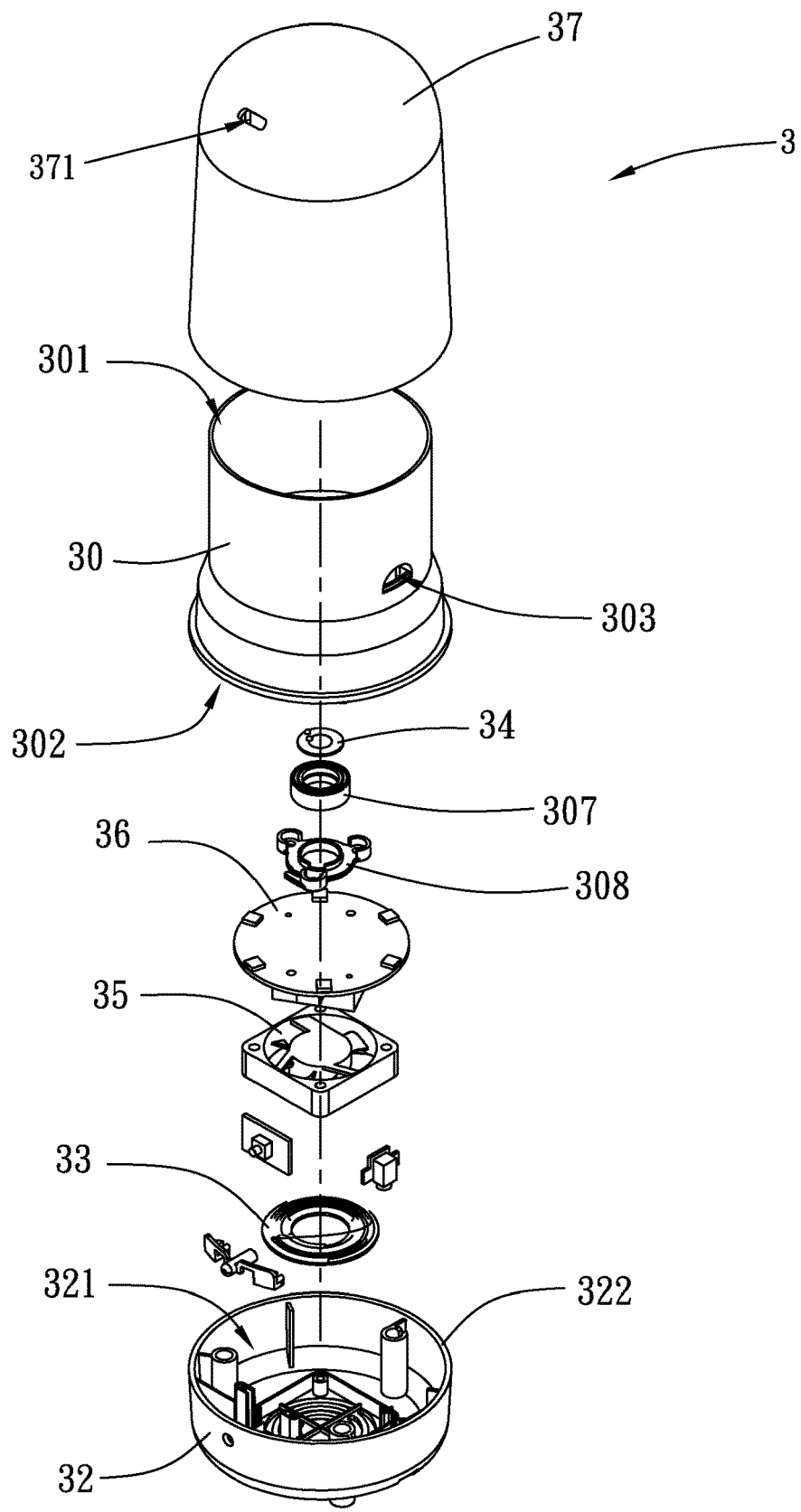
FIG. 5 is a perspective view showing the exploded components of the atomizer of the system and device according to the preferred embodiment of the present invention.
Figure 6:
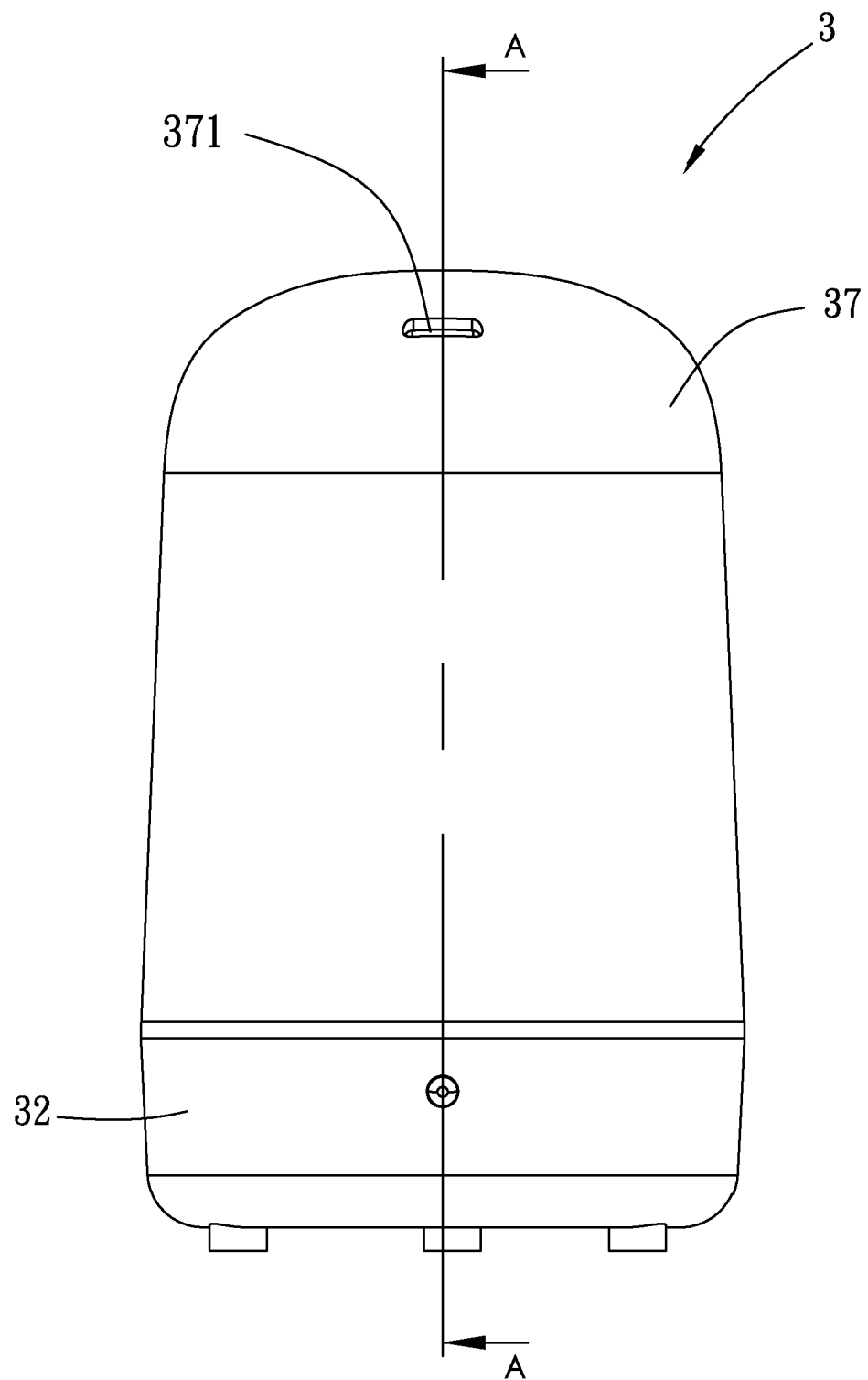
FIG. 6 is a side plan view showing the assembly of an atomizer of system and device according to another preferred embodiment of the present invention.
Figure 7:
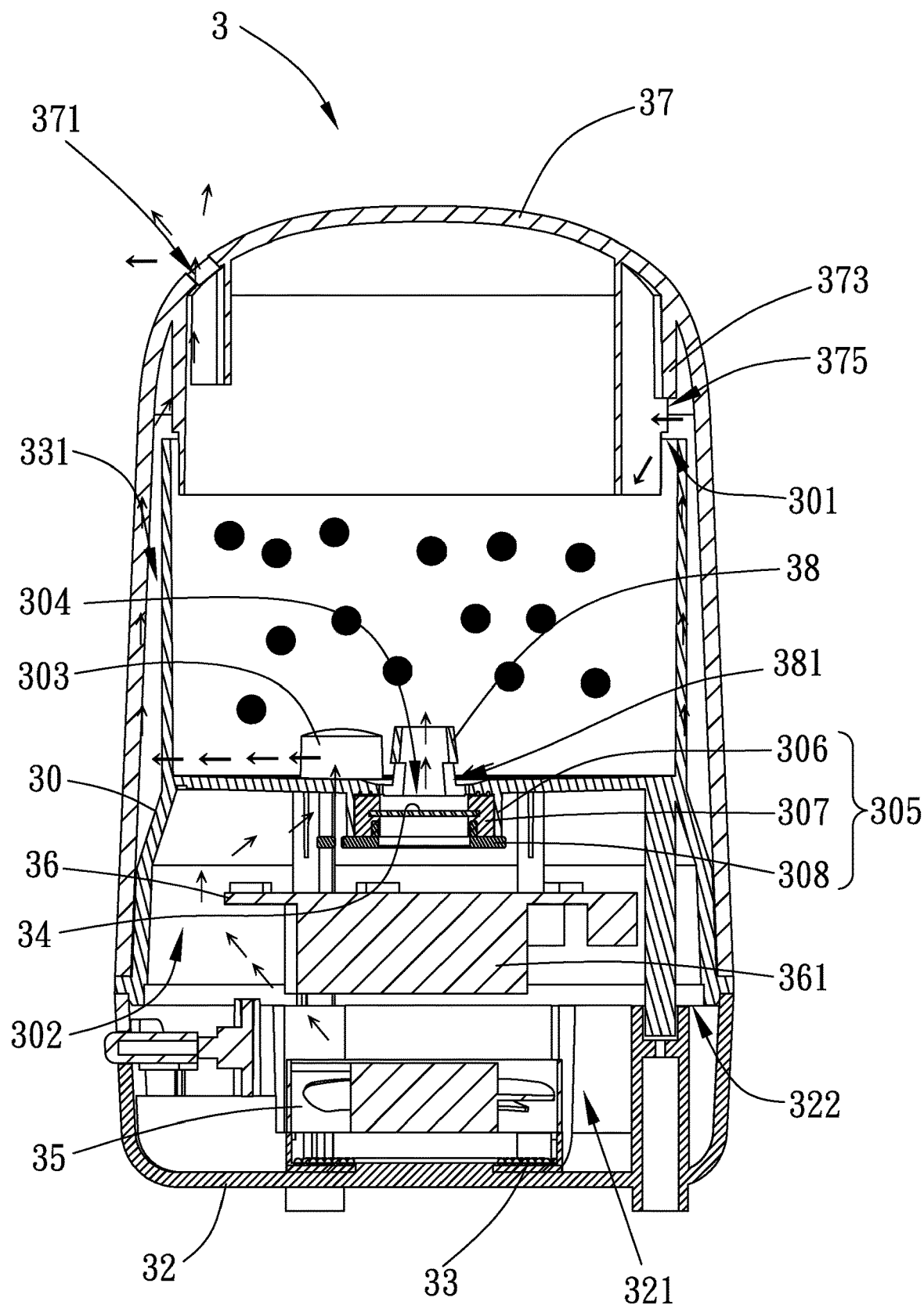
FIG. 7 is a cross sectional view taken along the line A-A of FIG. 6.

Referring to FIGS. 1, 5, and 7, the hollow waterproof structure 305 further has a trench 306, a seal ring 307, and a fixer 308, wherein a first end of the trench 306 extends downward from a top of the cap 37, and a second end of the trench 306 is connected with the fixer 308. The oscillator 34 is received in the seal ring 307, and the seal ring 307 is fitted into the trench 306, wherein the oscillator 34 corresponds to a lower end of the through orifice 304 so that the liquid flows into the oscillator 34 from the first groove 301 via the through orifice 304, the seal ring 307 stops the liquid flowing to the fan 35, and the fixer 308 closes a free end of the trench 306, such that the liquid does not flow out of the hollow waterproof structure 305 from the first groove 301 so as to protect the main control circuit, the wireless charging receiver or the air conveyor.

The liquid (not shown) is filled into the first groove 301, the wireless charging receiver 33 of the atomizer 3 is close to the electromagnetic signal sent by the wireless charger 1 so as to receive the electromagnetic signal and to convert the electromagnetic signal into the electric power for driving the oscillator 34 to oscillate and atomize the liquid, and the air conveyor 35 transports the air to diffuse scents of the liquid. The atomizer 3 does not have electric contacts so as to avoid electric shock or electric resistance of electrical wire. As desiring to refill the liquid, it is not necessary to remove an electrical plug of the atomizer 3 so as to clean the container and/or to refill the liquid, thus obtaining using safety of the atomizer 3.

The wireless charger and the wireless charging receiver are selected based on a variety of wireless charging standards, such as Wireless Power Consortium (i.e., Qi standard), Power Matters Alliance (PMA), and Alliance for Wireless Power (A4WP).

As shown in FIGS. 1-3, 5 and 8, the wireless charger 1 further includes at least one transmitting coil module 11, for example, the wireless charger 1 is electrically connected with multiple transmitting coil modules 11 so that the liquid atomizing system and device are electrically charged by using the multiple transmitting coil modules 11 or/and electrically charges the various mobile devices or terminal devices in the wireless manner.

Each of the at least one transmitting coil module 11 has a power circuit 13, a high-frequency oscillating circuit 15, and a high-frequency power amplifier circuit 17, wherein the power circuit 13 is electrically connected with the high-frequency oscillating circuit 15 and the high-frequency power amplifier circuit 17 so as to excite and transmit the electromagnetic waves. The wireless charging receiver 33 of the atomizer 3 includes a receiving coil module 331 which has a high-frequency rectification filter circuit 333 configured to auxiliary receive rectification voltage of the electric currents. In addition, the high-frequency rectification filter circuit 333 is electrically connected with the air conveyor 35.

Each transmitting coil module 11 further has a magnetic conductor and a transmitting control circuit. The receiving coil module 331 has a receiving control circuit or a rectification regulator circuit, and each transmitting coil module 11 produces the magnetic field which couples with the receiving coil module 331, such that the receiving coil module 331 is connected with magnetic field signals, and the receiving control circuit of the receiving coil module 331 converts the magnetic field signals into a power of the electricity applicable for the air conveyor 35.

As illustrated in FIG. 7, the atomizer 3 further includes a heat dissipator 360 connected on a bottom of the main control circuit 36 so as to dissipate a heat of the main control circuit 36, wherein the heat dissipator 360 is made of any one of metal material, ceramics, and silicone, wherein the meat material is aluminum or copper.

Figure 2:
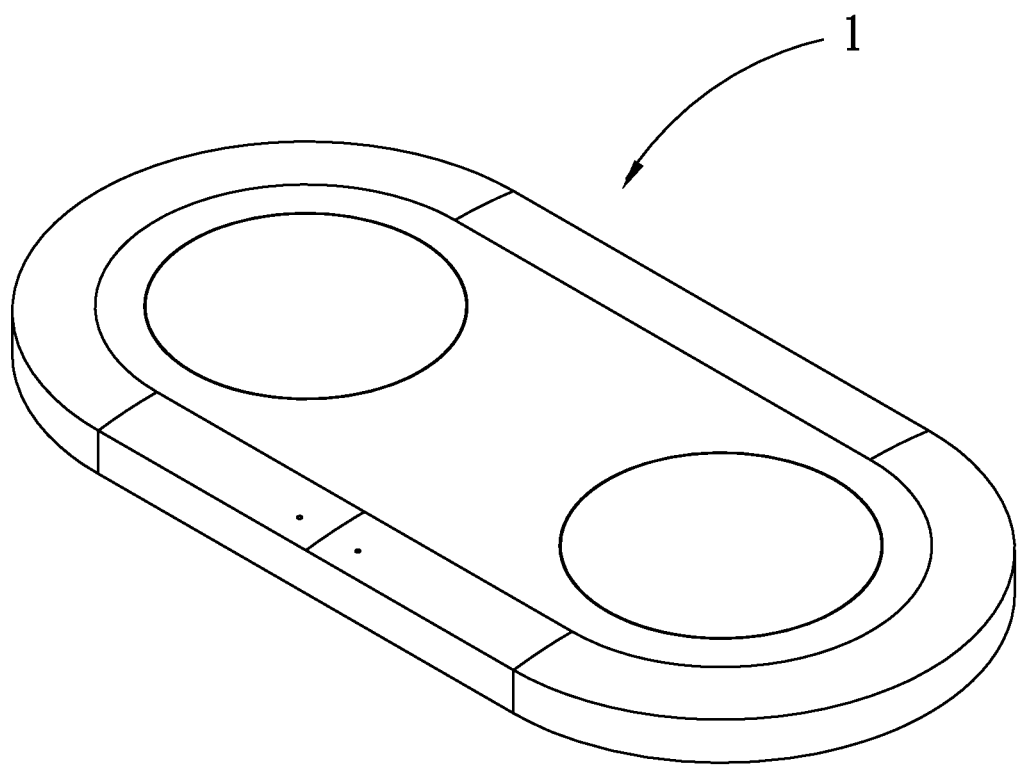
FIG. 2 is a perspective view showing the assembly of a wireless charger of the system and device according to the preferred embodiment of the present invention.
Figure 3:
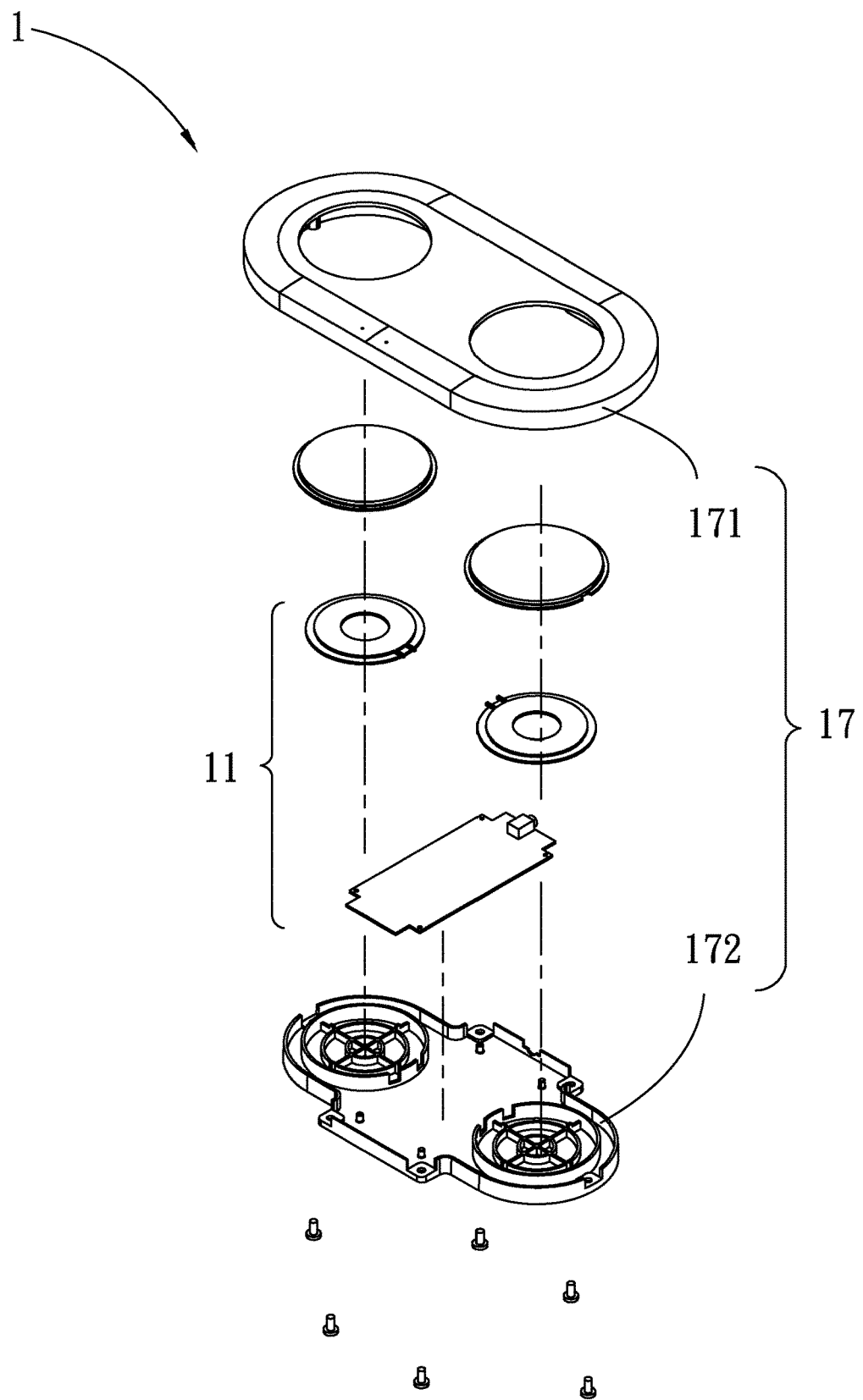
FIG. 3 is a perspective view showing the exploded components of the wireless charger of the system and device according to the preferred embodiment of the present invention.
Figure 4:
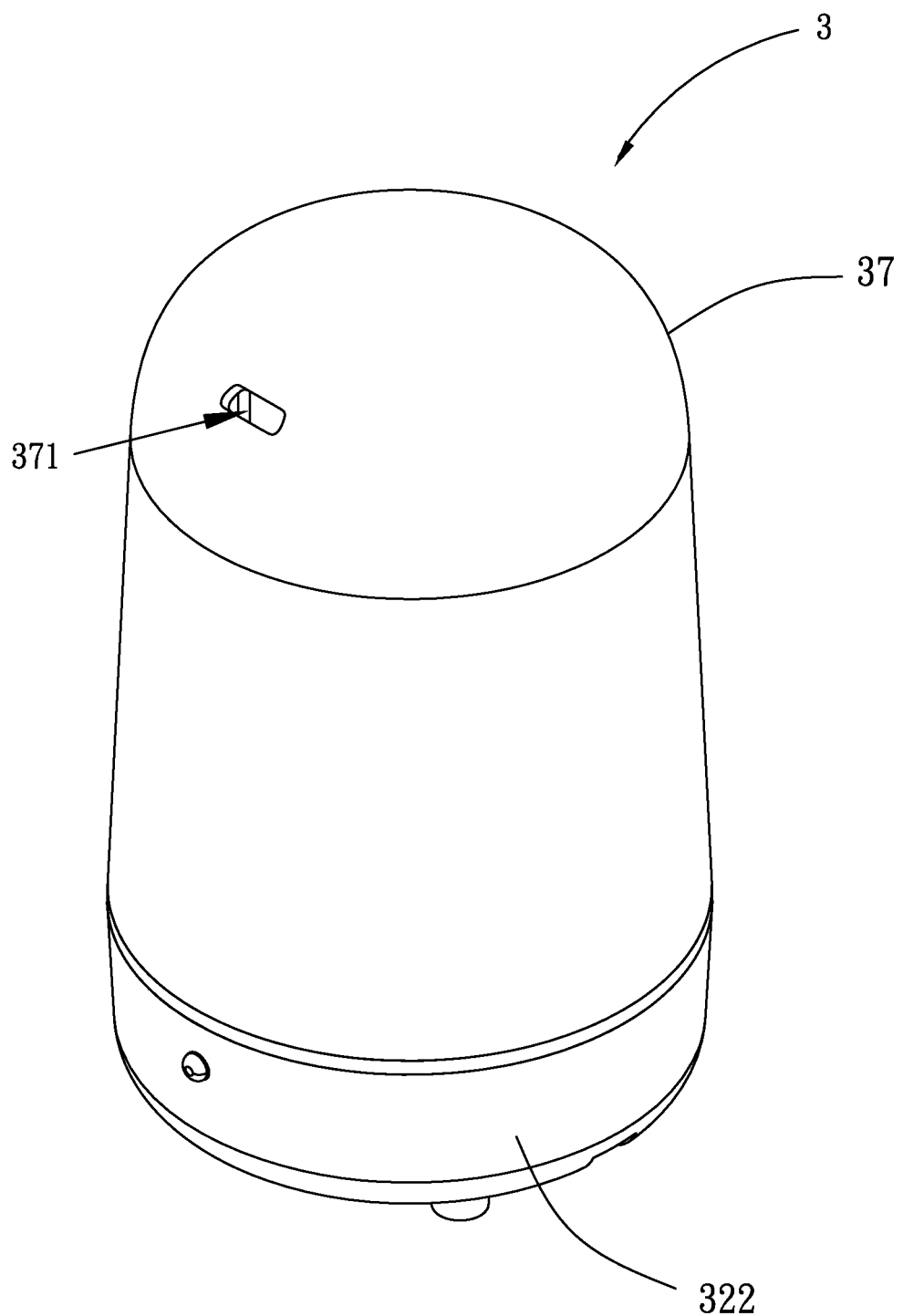
FIG. 4 is a perspective view showing the assembly of an atomizer of the system and device according to the preferred embodiment of the present invention.
Figure 8:
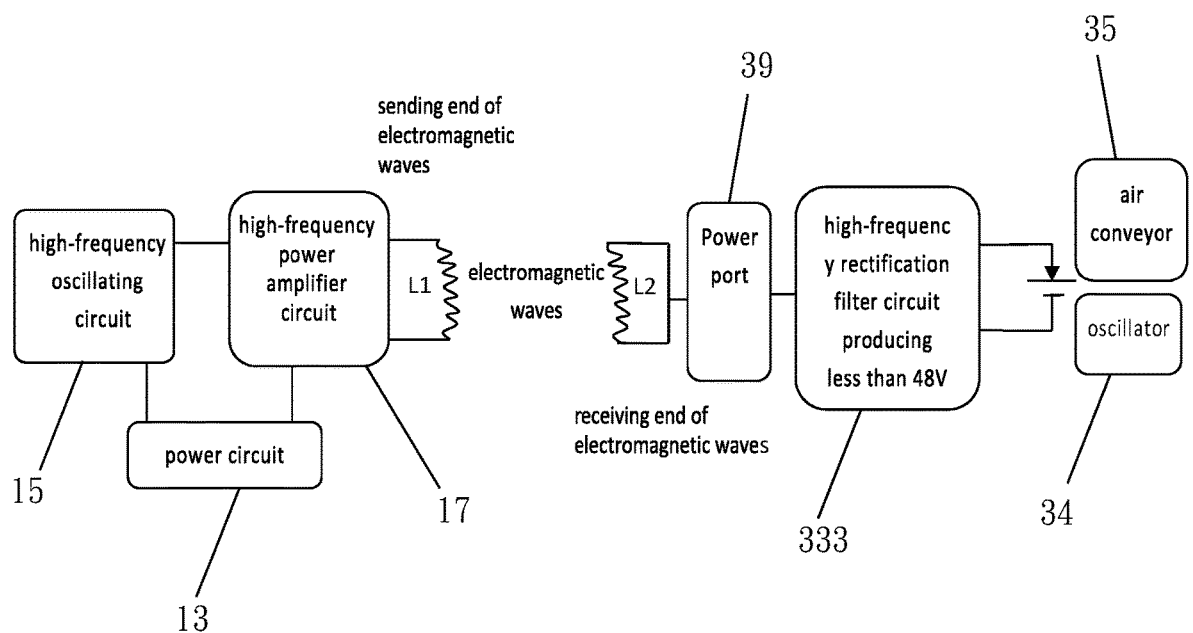
FIG. 8 is a block diagram showing the assembly of the device of FIG. 1.

With reference to FIGS. 2, 3 and 8, the wireless charger 1 of the liquid atomizing system and device includes a charge board 17 which has a first lid 171 and a second lid 172 connected with the first lid 172, wherein the at least one transmitting coil module 11 of the wireless charger 1 is fixed in the charge board 17. In this embodiment, two transmitting coil modules 11 are provided. In another embodiment, multiple transmitting coil modules 11 are provided, and the charge board 17 of the wireless charger 1 is electrically connected with the power source and the multiple transmitting coil modules 11 so that the liquid atomizing system and device are electrically charged by using the multiple transmitting coil modules 11 or/and electrically charges the various mobile devices or terminal devices in the wireless manner.

With reference to FIGS. 2, 3 and 8, the wireless charger 1 of the liquid atomizing system and device includes multiple transmitting coil modules 11 which are separately arranged in the charge board 17 and are parallelly connected so as to electrically charge mobile devices or terminal devices in the wireless manner. When the atomizer 3 is electrically charged, the multiple transmitting coil modules 11 electrically charge mobile phones, wireless mice, or calculators in the wireless manner.

Referring to FIGS. 1 and 7, the atomizer 3 of the liquid atomizing system and device further includes a built-in power interface 39 formed on a side of the container 30 and electrically connected with the main control circuit 36, the air conveyor 35, and the oscillator 34, such that the atomizer 3 is electrically connected with a power cable and the built-in power interface 39 so as to be electrically charged in a wired manner. The main control circuit 36 is configured to control the air conveyor 35 and the oscillator 34 to operate.

Figure 9:
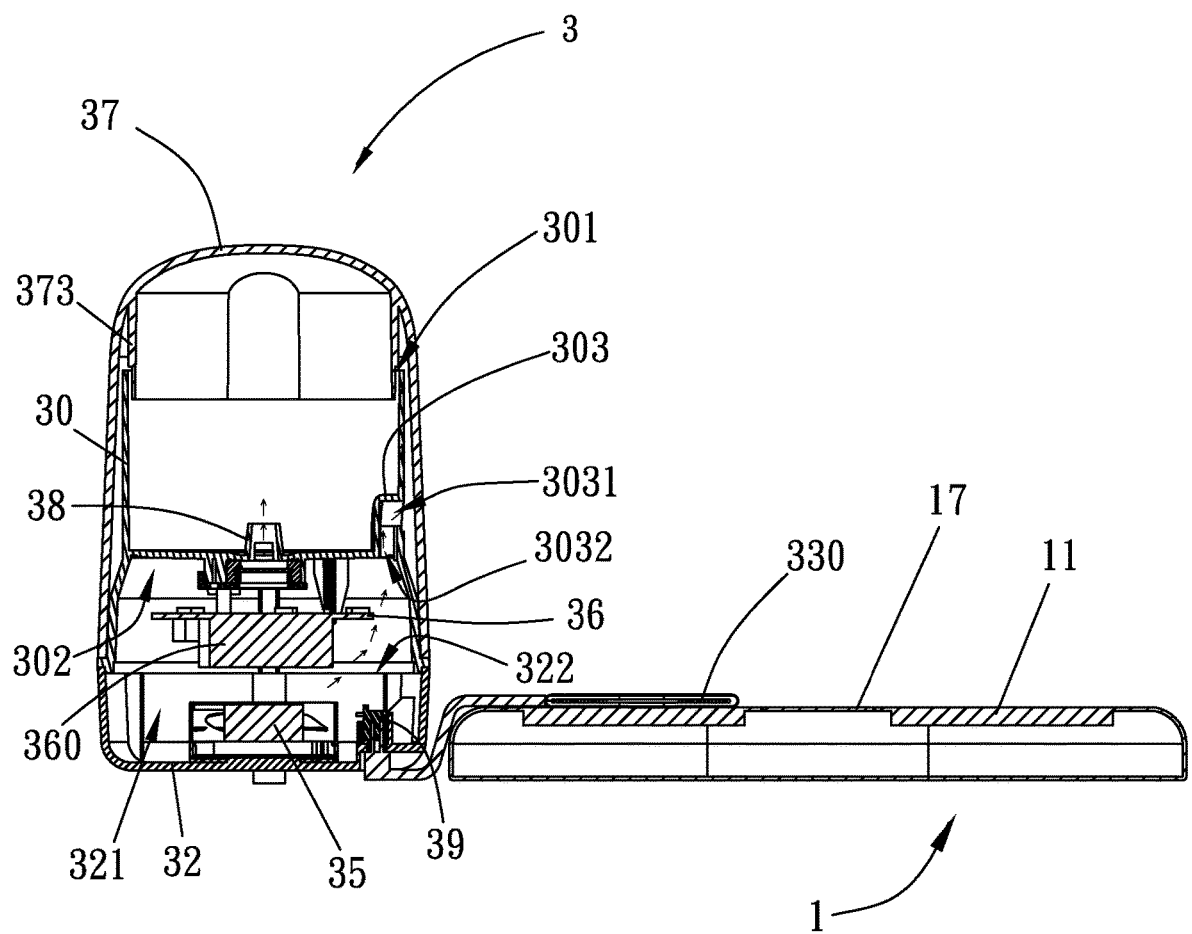
FIG. 9 is a cross sectional view showing the assembly of system and device according to another preferred embodiment of the present invention.
Figure 10:
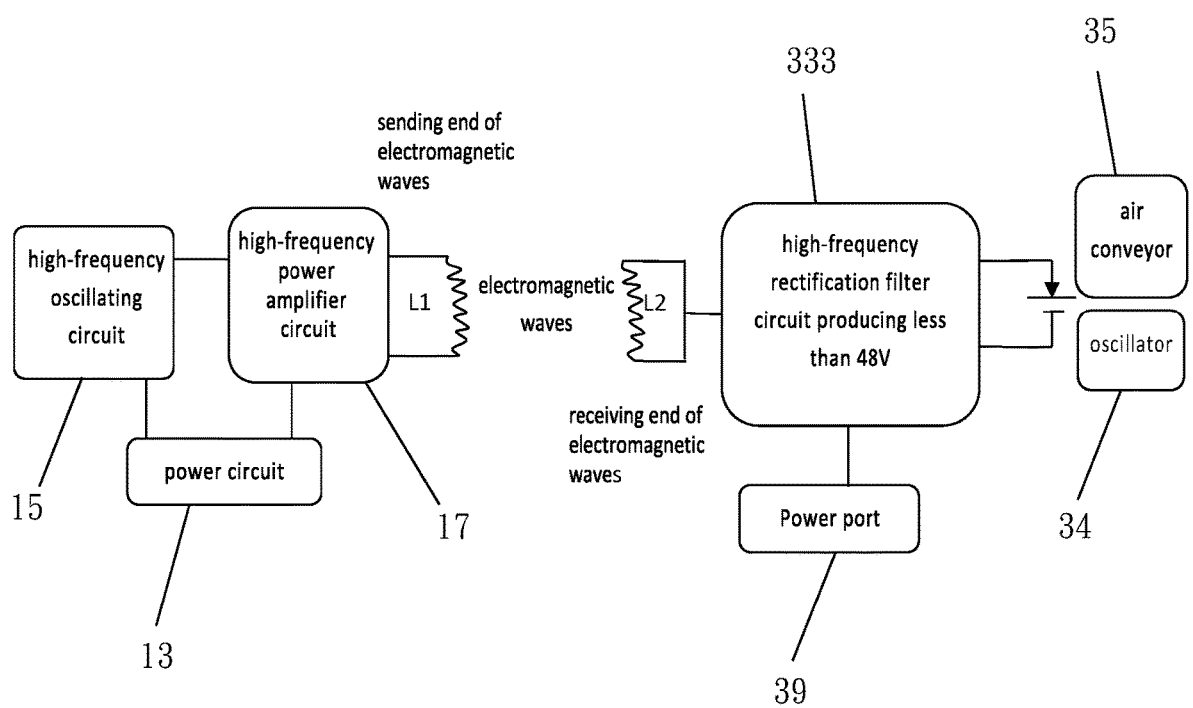
FIG. 10 is a block diagram showing the assembly of the device of FIG. 9.

As shown in FIGS. 9 and 10, in another embodiment, a liquid atomizing device with an externally wireless charging receiver 330 comprises an atomizer 3 which is electrically wireless connected outside the wireless charger 1 and is electrically charged in a wireless manner by the externally wireless charging receiver 330, wherein the atomizer 3 includes a built-in power interface 39 formed on the side of the atomizer 3 and electrically connected with the main control circuit 36, the air conveyor 35, and the oscillator 34, wherein the externally wireless charging receiver 330 is connected with the built-in power interface 39 by ways of an electrical wire, such that the atomizer 3 is electrically charged by using the externally wireless charging receiver 330 in the wired manner.

The wireless charger 1 is selected based on the variety of wireless charging standards, such as the Wireless Power Consortium (i.e., Qi standard), the Power Matters Alliance (PMA), and the Alliance for Wireless Power (A4WP). The externally wireless charging receiver 330 is selected based on the variety of wireless charging standards, such as the Wireless Power Consortium (i.e., Qi standard), the Power Matters Alliance (PMA), and the Alliance for Wireless Power (A4WP).

With reference to FIGS. 9 and 10, in another embodiment, an external liquid atomizing device electrically charged in a wireless manner comprises: an atomizer 3 which is electrically wireless connected outside the wireless charger 1 and is electrically charged in the wireless manner by using the wireless charging receiver 33, wherein the atomizer 3 includes a container 30, a case 32, an externally wireless charging receiver 330, an oscillator 34, an air conveyor 35, a main control circuit 36, a cap 37, and a built-in power interface 39. The case 32 has an accommodation chamber 321 defined therein and has an opening 322 formed on a top of the accommodation chamber 321, the externally wireless charging receiver 330 and the air conveyor 35 are accommodated in the accommodation chamber 321 of the case 32, wherein the built-in power interface 39 is accommodated on a side of the accommodation chamber 321, a first side of the built-in power interface 39 is electrically connected with the main control circuit 35, the air conveyor 35 and the oscillator 34, and a second side of the built-in power interface 39 is electrically connected with the externally wireless charging receiver 330.

The container 30 abuts against the top of the case 32 so as to shield the opening 322 of the accommodation chamber 321. The container 30 includes a first groove 301, a second groove 302, an air guide portion 303, a through orifice 304, and a hollow waterproof structure 305, wherein the first groove 301 extends to the second groove 302 which communicates with the accommodation chamber 321, and the through orifice 304 is defined between a bottom of the first groove 301 and a top of the second groove 303. The hollow waterproof structure 305 closes the through orifice 304 from a top of the second groove 302, the oscillator 34 is received in the hollow waterproof structure 305 and corresponds to the through orifice 304, and the main control circuit 36 is accommodated in the second groove 302.

The cap 37 has a nozzle 371 defined on a top thereof and covers the container 30 and the first groove 301, the air guide portion 303 is arranged on a side of the first groove 301 and has an outlet 3031 and an inlet 3033, wherein the outlet 3031 communicates with an outer wall of the container 30 and an inner wall of the cap 37, and the inlet 3033 is in communication with the second groove 303.

The externally wireless charging receiver 330 is electrically connected with the second side of the built-in power interface 39 by using an electrical wire, wherein the externally wireless charging receiver 330 is close to the electromagnetic signals of a wireless charger 1 so as to induce the electromagnetic signals.

As shown in FIGS. 9 and 10, the atomizer 3 further includes a receiving coil module 331 which has a high-frequency rectification filter circuit 333 configured to auxiliary receive rectification voltage of the electric currents, the receiving coil module 331 is connected with the second side of the built-in power interface 39 by using another electrical wire.

Referring to FIGS. 1-7, a liquid atomizing device comprises: a wireless charger 1 configured to converts electric currents into electromagnetic signal; an atomizer 3 including a wireless charging receiver 33, wherein the wireless charging receiver 33 of the atomizer 3 is configured to receive electromagnetic signal of the wireless charger 1 and to convert the electromagnetic signal into electric power for driving the atomizer 3 to atomize liquid to micro water molecule and to deliver the micro water molecule to an external environment.

While the preferred embodiments of the invention have been set forth for the purpose of disclosure, modifications of the disclosed embodiments of the invention as well as other embodiments thereof may occur to those skilled in the art. The scope of the claims should not be limited by the preferred embodiments set forth in the examples, but should be given the broadest interpretation consistent with the description as a whole.

What is claimed is:

1. A liquid atomizing system electrically charged in a wireless manner comprising:

a liquid, a wireless charger, and an atomizer including a wireless charging receiver;

wherein the liquid is filled in the atomizer, and the wireless charger is electrically connected with a power source so that an electric power is inputted to the wireless charger from the power source to produce a magnetic field and to send an electromagnetic signal, thus transmitting energy by using the magnetic field;

wherein the wireless charging receiver of the atomizer is close to the electromagnetic signal sent by the wireless charger so as to receive the electromagnetic signal and to convert the electromagnetic signal into the electric power for driving the atomizer to atomize the liquid to micro water molecule and to deliver the micro water molecule to an external environment;

the atomizer includes a container, a case, an oscillator, an air conveyor, a main control circuit, and a cap;

the case has an accommodation chamber defined therein and has an opening formed on a top of the accommodation chamber, the wireless charging receiver and the air conveyor are accommodated in the accommodation chamber of the case;

the container abuts against a top of the case so as to shield the opening of the accommodation chamber, the container includes a first groove, a second groove, an air guide portion, a through orifice, and a hollow waterproof structure, wherein the first groove extends to the second groove which communicates with the accommodation chamber, and the first groove receives the liquid, the through orifice is defined between a bottom of the first groove and a top of the second groove, the hollow waterproof structure closes the through orifice from the top of the second groove, the oscillator is received in the hollow waterproof structure and corresponds to the through orifice;

the main control circuit is accommodated in the second groove;

the cap has a nozzle defined on a top thereof and covers the container and the first groove, the air guide portion is arranged on a side of the first groove and has an outlet and an inlet, wherein the outlet communicates with an outer wall of the container and an inner wall of the cap, and the inlet is in communication with the second groove; and the main control circuit is electrically connected with the wireless charging receiver, the oscillator, and the air conveyor.

2. The liquid atomizing system as claimed in claim 1, wherein the cap has a shielding extension extending downward from a top of an inner wall of the cap and communicating with the first groove, and the cap further has an aperture defined on a side of the shielding extension adjacent to the first groove, wherein the aperture communicates with the air guide portion and the outlet.

3. The liquid atomizing system as claimed in claim 2, wherein the wireless charger includes at least one transmitting coil module, and each of the at least one transmitting coil module has a power circuit, a high-frequency oscillating circuit, and a high-frequency power amplifier circuit, wherein the power circuit is electrically connected with the high-frequency oscillating circuit and the high-frequency power amplifier circuit; the wireless charging receiver of the aroma diffuser includes a receiving coil module which has a high-frequency rectification filter circuit which is electrically connected with the air conveyor.

4. The liquid atomizing system as claimed in claim 3, wherein the wireless charger further includes multiple transmitting coil modules electrically connected therewith.

5. A liquid atomizing device electrically charged in a wireless manner comprising:
   an atomizer including a container, a case, a wireless charging receiver, an oscillator, an air conveyor, a main control circuit, and a cap;
   wherein the case has an accommodation chamber defined therein and has an opening formed on a top of the accommodation chamber, the wireless charging receiver and the air conveyor are accommodated in the accommodation chamber of the case;
   wherein the container abuts against a top of the case so as to shield the opening of the accommodation chamber, the container includes a first groove, a second groove, an air guide portion, a through orifice, and a hollow waterproof structure, wherein the first groove extends to the second groove which communicates with the accommodation chamber, and the first groove receives the liquid, the through orifice is defined between a bottom of the first groove and a top of the second groove, the hollow waterproof structure closes the through orifice from a top of the second groove, the oscillator is received in the hollow waterproof structure and corresponds to the through orifice;
   wherein the main control circuit is accommodated in the second groove; and
   wherein the cap has a nozzle defined on a top thereof and covers the container and the first groove, the air guide portion is arranged on a side of the first groove and has an outlet and an inlet, wherein the outlet communicates with an outer wall of the container and an inner wall of the cap, and the inlet is in communication with the second groove; and
   wherein the main control circuit is electrically connected with the wireless charging receiver, the oscillator, and the air conveyor.

6. The liquid atomizing device as claimed in claim 5, wherein the cap has a shielding extension extending downward from a top of an inner wall of the cap and communicating with the first groove, and the cap further has an aperture defined on a side of the shielding extension adjacent to the first groove, wherein the aperture communicates with the air guide portion and the outlet.

7. The liquid atomizing device as claimed in claim 6 further comprising a wireless charger which further includes at least one transmitting coil module, wherein each of the at least one transmitting coil module has a power circuit, a high-frequency oscillating circuit, and a high-frequency power amplifier circuit, wherein the power circuit is electrically connected with the high-frequency oscillating circuit and the high-frequency power amplifier circuit; the wireless charging receiver of the aroma diffuser includes a receiving coil module which has a high-frequency rectification filter circuit which is electrically connected with the air conveyor.

8. The liquid atomizing device as claimed in claim 7, wherein the wireless charger includes a charge board which has a first lid and a second lid connected with the first lid, wherein the at least one transmitting coil module of the wireless charger is fixed in the charge board.

9. The liquid atomizing device as claimed in claim 8, wherein the wireless charger further includes multiple transmitting coil modules which are separately arranged in the charge board and are electrically connected with the wireless charger.

10. The liquid atomizing device as claimed in claim 5, wherein the atomizer further includes a built-in power interface formed on a side of the case and electrically connected with the air conveyor.

11. The liquid atomizing device as claimed in claim 5, wherein the atomizer further includes a hollow pipe formed on and communicating with the through orifice of the first groove; and the atomizer further includes a hole formed on a bottom of the hollow pipe communicating with the through orifice and the hollow pipe.

12. The liquid atomizing device as claimed in claim 11, wherein the hollow waterproof structure further has a trench, a seal ring, and a fixer; wherein a first end of the trench extends downward from a top of the cap, and a second end of the trench is connected with the fixer; the oscillator is received in the seal ring, and the seal ring is fitted into the trench, wherein the oscillator corresponds to a lower end of the through orifice.

13. A liquid atomizing device with an externally wireless charging receiver comprising an atomizer which is electrically wireless connected outside a wireless charger and is electrically charged in a wireless manner by using the externally wireless charging receiver;
   wherein the atomizer includes a container, a case, the externally wireless charging receiver, an oscillator, an air conveyor, a main control circuit, a cap, and a built-in power interface;
   wherein the case has an accommodation chamber defined therein and has an opening formed on a top of the accommodation chamber;
   wherein the externally wireless charging receiver and the air conveyor are accommodated in the accommodation chamber of the case;
   wherein the built-in power interface is accommodated on a side of the accommodation chamber, a first side of the built-in power interface is electrically connected with the main control circuit, the air conveyor and the oscillator, and a second side of the built-in power interface is electrically connected with the externally wireless charging receiver;
   wherein the container abuts against a top of the case so as to shield the opening of the accommodation chamber, the container includes a first groove, a second groove, an air guide portion, a through orifice, and a hollow waterproof structure, wherein the first groove extends to the second groove which communicates with the accommodation chamber, and the through orifice is defined between a bottom of the first groove and a top of the second groove, the hollow waterproof structure closes the through orifice from a top of the second groove, the oscillator is received in the hollow waterproof structure and corresponds to the through orifice;
   wherein the main control circuit is accommodated in the second groove; and
   wherein the cap has a nozzle defined on a top thereof and covers the container and the first groove, the air guide portion is arranged on a side of the first groove and has an outlet and an inlet, wherein the outlet communicates with an outer wall of the container and an inner wall of the cap, and the inlet is in communication with the second groove.

* * * * *